United States Patent
Hideshima et al.

(10) Patent No.: US 7,566,129 B2
(45) Date of Patent: Jul. 28, 2009

(54) OPHTHALMOLOGIC APPARATUS

(75) Inventors: Masayuki Hideshima, Tokyo (JP);
Kazuo Nunokawa, Tokyo (JP); Makoto Fujino, Tokyo (JP); Yoichiro Iwa, Tokyo (JP); Akemi Miwa, Tokyo (JP); Yoshiaki Goto, Tokyo (JP); Gaku Takeuchi, Tokyo (JP); Takao Tanabe, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 229 days.

(21) Appl. No.: 11/767,456

(22) Filed: Jun. 22, 2007

(65) Prior Publication Data
US 2007/0296919 A1    Dec. 27, 2007

(30) Foreign Application Priority Data
Jun. 22, 2006    (JP)    ............................ 2006-172769

(51) Int. Cl.
*A61B 3/14*    (2006.01)
*A61B 3/10*    (2006.01)

(52) U.S. Cl. ...................................... 351/206; 351/205

(58) Field of Classification Search ................. 351/204, 351/205, 206, 208, 210, 214, 221
See application file for complete search history.

(56) References Cited

U.S. PATENT DOCUMENTS 5,943,115 A    8/1999    Ferguson 7,290,881 B2 *    11/2007    Matsumoto ................. 351/214
7,370,966 B2 *    5/2008    Fukuma et al. ............. 351/205
2005/0254008 A1    11/2005    Ferguson et al.

FOREIGN PATENT DOCUMENTS

EP    1480552 A    12/2004
WO    WO 99/23936 A    2/1999

OTHER PUBLICATIONS

Extended European Search Report from Application No. 07012047.2-1265 dated Oct. 9, 2007.

\* cited by examiner

*Primary Examiner*—Hung X Dang
*Assistant Examiner*—Tuyen Q Tra
(74) *Attorney, Agent, or Firm*—Knobbe Martens Olson & Bear LLP

(57) ABSTRACT

An ophthalmologic apparatus is disclosed. In one aspect, the apparatus includes an ocular fundus photographing systems for forming an ocular fundus image of the examined eye, based on a reflective beam from the ocular fundus of the examined eye, and an ocular fundus tracking controller for detecting a gaze direction of the examined eye by receiving the reflective beam reflected at a reflective region of an illumination region illuminated on the ocular fundus and for tracking the ocular fundus based on the detection results of the gaze direction. The ocular fundus tracking controller may include scanning mirrors for scanning an area to detect a reflective beam from the ocular fundus, tracking mirrors for controlling tracking to the ocular fundus, an objective lens disposed opposite to the examined, and an offset mirror M19 for adjusting a detection axis in a gaze direction.

4 Claims, 6 Drawing Sheets

OPHTHALMOLOGIC APPARATUS

CROSS-REFERENCE TO RELATED APPLICATIONS

This application has related subject matter to U.S. application Ser. No. 11/767423 filed on the same date. This application claims priority from Japanese Patent Application No. 2006-172769, filed with the Japanese Patent Office on Jun. 22, 2006, the contents of which are incorporated herein by reference in their entirety.

BACKGROUND OF THE INVENTION

1. Field of the Invention

The present invention is related to an opthalmologic apparatus that includes an ocular fundus tracking controller for detecting a direction of gaze of an examined eye and following an ocular fundus imaging system in the direction of gaze, thereby photographing an ocular fundus with high resolution.

2. Description of the Related Technology

A conventional ocular fundus camera produces a deterioration in an ocular fundus image photographed because of optical aberration owned by the tested eye. Accordingly, the ocular fundus camera has a disadvantage that an clear image of the ocular fundus having high magnification cannot be obtained.

Owing to this, these days, a technology for photographing an ocular fundus image is proposed by which the optical aberration of the tested eye is measured and compensated by using a compensation optical system based on the measured results. The technology can eliminate an influence caused by the optical aberration of the tested eye to produce a higher magnification of the ocular fundus image compared with the conventional technique.

However, the conventional opthalmologic apparatus has difficulties in photographing an ocular fundus image with much higher magnification and higher resolution applied to a visual cell level. One of the difficulties is a fixation micro-movement of an eyeball. That is, the eyeball always continues a micro-movement called a fixation micro-movement, which always moves a gaze direction of the eye. Accordingly, since an ocular fundus image to be photographed is oscillating and causes a blur, it is essential to remove an influence of the fixation micro-movement in order to take a picture of the ocular fundus image with much higher resolution.

So as to get rid of the blur of the ocular fundus image in a difference of the gaze direction of the eye, an opthalmologic apparatus has been proposed in which the gaze direction of the examined eye is detected and tracking is carried out with respect to the ocular fundus based on the detection results. See, for example, U.S. Pat. No. 5,943, 115.

According to the technology disclosed in the US patent, in order to detect a gaze direction of the tested eye on the ocular fundus, a detection beam of a infinitesimal region close to the point light source is projected to the ocular fundus for scanning so that a circular locus is drawn on the ocular fundus. A reflective beam at the ocular fundus of the detection beam is received to detect the gaze direction of the tested eye, which controls a pair of tracking mirror from.

The optical system projects a detection beam on the ocular fundus of the examined eye through the order of a detection light source, a vibration reflective mirror (scanning mirror) for scanning the detection beam in a circular locus on the ocular fundus, a tracking mirror for controlling tracking according to the gaze direction of the examined eye that is detected, and an objective lens. Then, the optical system receives a reflective beam from the ocular fundus via the objective lens, the vibration reflective mirror (scanning mirror) and the tracking mirror.

On the other hand, an area to which a detection beam is projected and at which a reflective beam is detected may be a characteristic portion brighter than the environment, for example, an optic disc. Since a desired region of the ocular fundus other than the characteristic portion should be photographed, projection of the detection beam and shift of the axis of the light receiving system (corresponding to the detection axis of the gaze direction) are arbitrarily adjusted with respect to the optical axis for photographing the ocular fundus.

Because of this, the US patent discloses a structure in which the detection optical axis of the vibration reflection mirror (scanning mirror) to scan the detection beam is shifted by a predetermined amount to shift the detection axis of the gaze direction.

If the technology of the US patent is applied to an opthalmologic apparatus having high magnification, the detection axis of the gaze direction can be shifted in the high magnification observation region. However, when shifting the detection axis of the gaze direction outside the observation region, there is a disadvantage that an effective aperture of the ocular fundus high magnification should be much higher than is necessary. There is a need for a opthalmologic apparatus that can solve the disadvantage.

SUMMARY OF CERTAIN INVENTIVE ASPECTS

Aspects of the invention provide an opthalmologic apparatus that satisfies the need. Certain aspects include an opthalmologic apparatus that can adjust a detection optical axis in the gaze direction to a large extent and even to outside a region of ocular fundus high magnification observation, and photograph the ocular fundus with high magnification and high resolution, although an effective aperture of a photographing lens for the ocular fundus high magnification observation.

One aspect is an opthalmologic apparatus comprises an ocular fundus photographing system that forms an image of an ocular fundus of a tested eye on a photographing apparatus based on a reflective beam from the ocular fundus; and an ocular fundus tracking controller that detects a light beam from the ocular fundus, reflected at a reflective region of an illuminated region on the ocular fundus to detect a gaze direction of the tested eye, and performs tracking with respect to the ocular fundus based on the detection result of the gaze direction. The ocular fundus tracking controller comprises a scanning mirror for scanning an area on which a detection beam projected on the ocular fundus is detected or a reflective beam from the ocular fundus is detected; a tracking mirror for controlling tracking to the ocular fundus; an objective lens disposed opposite to the tested eye; and an offset mirror positioned between the objective lens and the tracking mirror outside of a photographing optical path for the ocular fundus, for adjusting a detection axis of the gaze direction.

The reflective beam from the ocular fundus may proceed to the photographing apparatus not through the offset mirror after entering the tracking mirror.

The ocular fundus photographing system may include a compensation optical system for compensating optical aberration of the tested eye.

An opthalmologic apparatus may further comprise an illumination beam for photographing the ocular fundus and a detection beam for detecting the gaze direction of the tested eye, the illumination beam having a wavelength that is different from that of the detection beam.

BRIEF DESCRIPTION OF THE DRAWINGS

These and other features, aspects, and advantages of the present invention will become better understood with regard to the following description, appended claims, and accompanying drawings.

DETAILED DESCRIPTION OF CERTAIN INVENTIVE EMBODIMENTS

Figure 1:
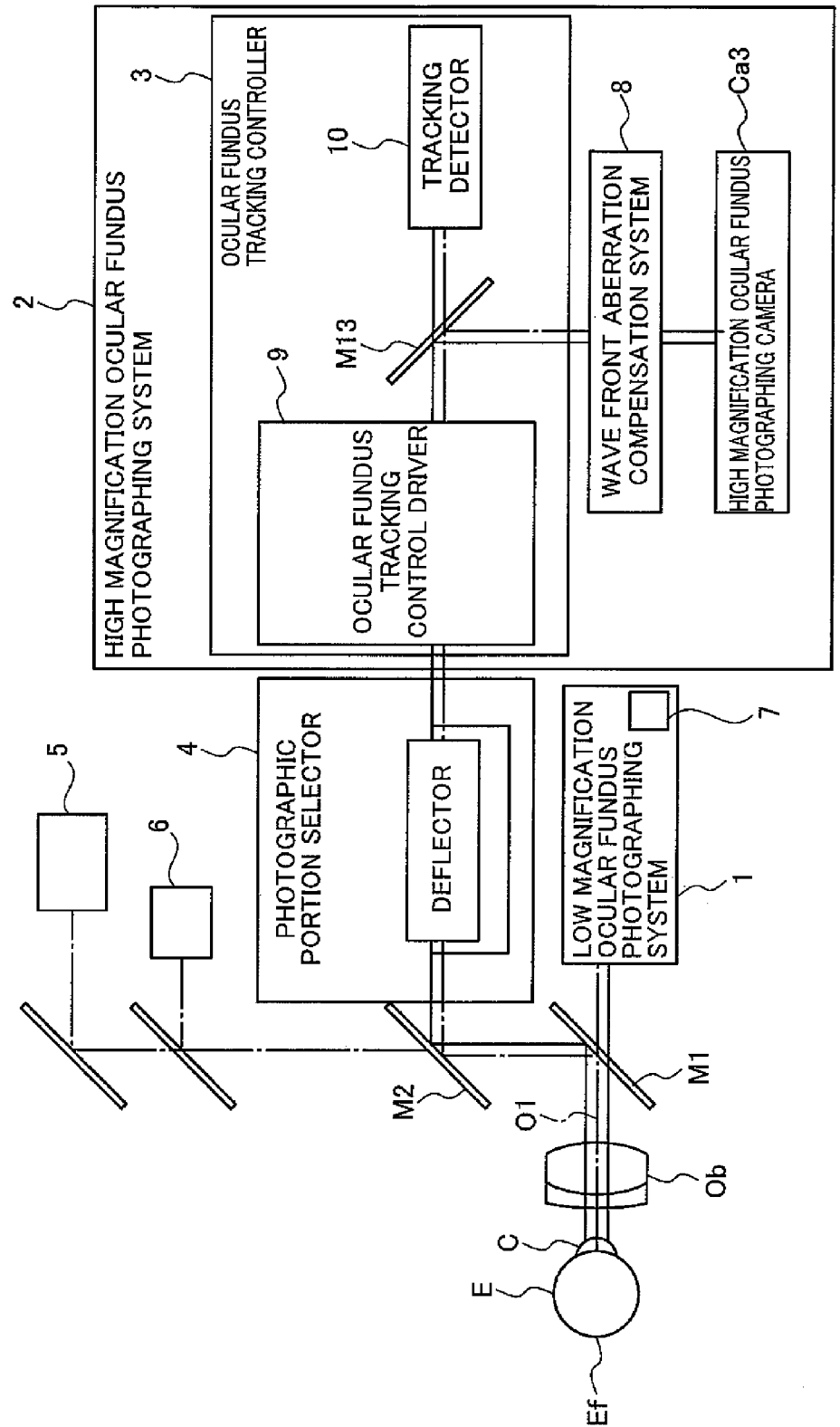
FIG. 1 is a block diagram illustrating an opthalmologic apparatus in accordance with an embodiment the present invention.

Embodiments of an opthalmologic apparatus in accordance with the present invention will be discussed referring to the drawings.

FIG. 1 is a block diagram illustrating an opthalmologic apparatus in accordance with the present invention. The opthalmologic apparatus includes a low magnification ocular fundus photographing system 1 for observing an ocular fundus Ef of the examined eye E, a high magnification ocular fundus photographing system 2 for photographing the ocular fundus Ef of the examined eye E, an ocular fundus tracking controller 3 for following the high magnification ocular fundus photographing system 2 to the gaze direction of the examined eye E, and a photographic portion selector 4 for selecting a photographic portion.

Figure 2:
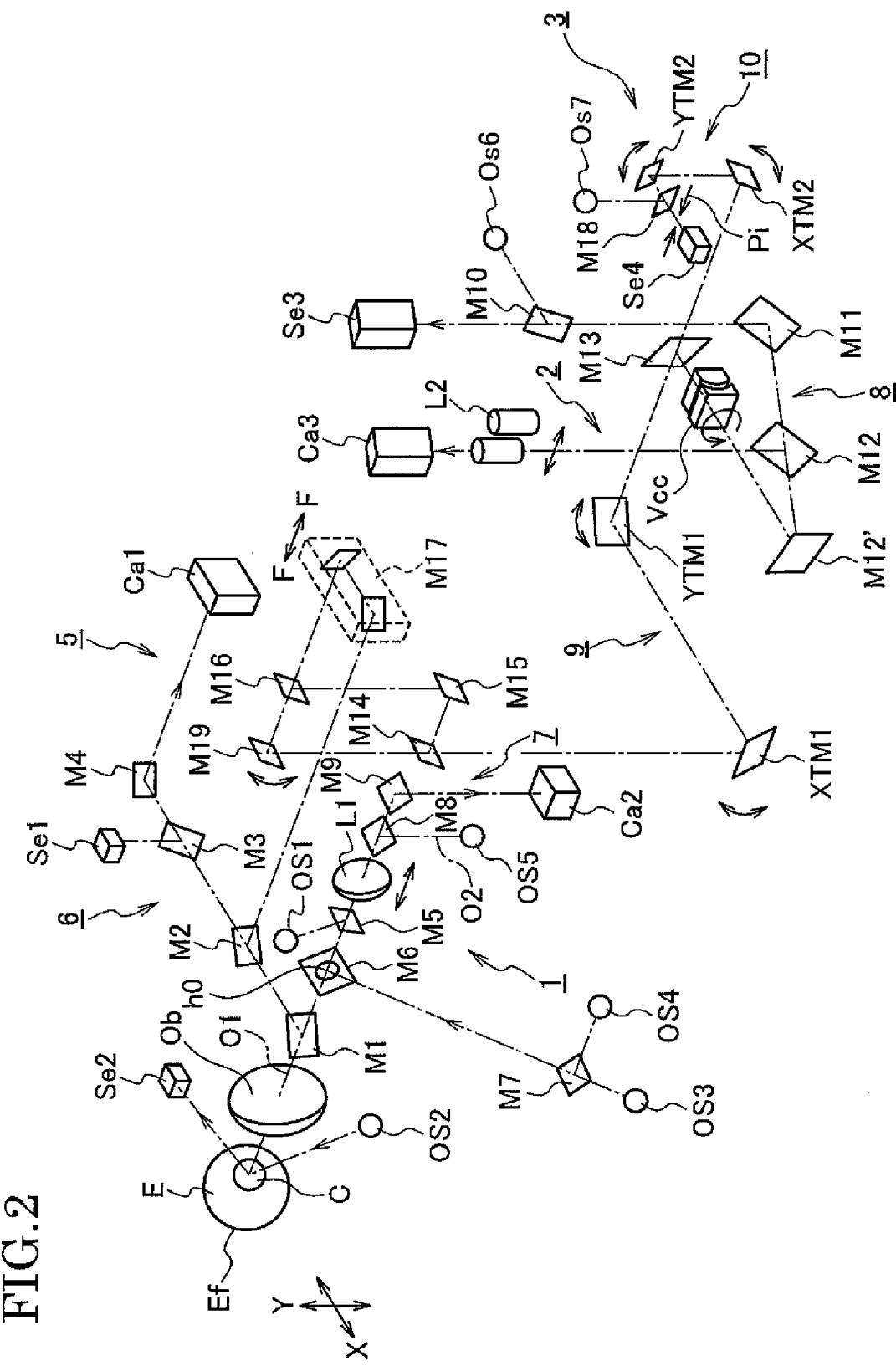
FIG. 2 is a detailed view illustrating an optical system of the opthalmologic apparatus shown in FIG. 1.

FIG. 2 is a detailed view illustrating an optical system of the opthalmologic apparatus shown in FIG. 1. The optical system includes an object lens Ob positioned in front of the tested eye E, the low magnification ocular fundus photographing system 1, the high magnification ocular fundus photographing system 2, an anterior eye segment observation system 5, an alignment detection system 6, a fixation target projection system 7, a wave front aberration compensation system 8, an ocular fundus tracking control driver 9, and a tracking detector 10.

Anterior Eye Segment Observation System 5

The anterior eye segment observation system 5 includes an anterior eye segment illumination source (not shown) for illuminating an anterior eye segment of the tested eye E and an anterior eye segment observation camera Ca1. Between the anterior eye segment of the tested eye E and the anterior eye segment observation camera Ca1, there exist an objective lens Ob, a half mirror M1, wavelength selection mirrors M2 and M3, and a total reflection mirror M4.

The anterior eye segment illumination source has wavelength $\lambda=700$ nm that is used as an anterior eye segment illumination light. The half mirror M1 reflects half of the light beams of wavelength 700 nm and transmits half of the light beams, respectively. The wavelength selection mirror M2 transmits all of the light beams from $\lambda=700$ nm to 770 nm, and reflects the light beams from $\lambda=500$ nm to 700 nm and from $\lambda=800$ nm to 1100 nm. The wavelength selection mirror M3 transmits half of the light beams of wavelength $\lambda=770$ nm and reflects half of the light beams, and transmits all of the light beams $\lambda=700$ nm.

The anterior eye segment illumination light beams are reflected at the anterior eye segment, focused by the object lens Ob, and led to the half mirror M1. Then, the anterior eye segment illumination light beams are deflected toward the wave selection mirror M2 by the half mirror M1, transmit through the wave selection mirrors M2 and M3, and are led to the total reflection mirror M4. Moreover, the anterior eye segment illumination light beams are led to the anterior eye segment observation camera Ca1 by the total reflection mirror M4, in which an anterior eye segment image of the tested eye E is formed.

While an observer or photographer observes, on a monitor, the anterior eye segment image focused in the anterior eye segment observation camera Ca1, he moves the opthalmologic apparatus by a manual operation to perform an alignment of the apparatus itself with respect to the tested eye E.

Alignment Detection System 6

The alignment detection system 6 includes an X-Y alignment detection light source Os1, an alignment mirror M5, an X-Y alignment sensor Se1, a Z alignment detection light source Os2, and a Z alignment sensor Se2.

Between the half mirror M1 and the alignment mirror M5, there exists a mirror M6 having a hole h0 therein. The alignment mirror M5 totally reflects the light beam of wavelength $\lambda=770$ nm, and totally transmits the light beams below wavelength $\lambda=700$ nm and over wavelength $\lambda=800$ nm.

LED's of wavelength $\lambda=770$ nm are used as the X-Y alignment detection light source Os1 and the Z alignment detection light source Os2. PSD's (semiconductor position detector) are used as the X-Y alignment sensor Se1 and the Z alignment sensor Se2.

A X-Y alignment detection light beam from the X-Y alignment detection light source Os1 is reflected by the alignment mirror M5 to pass through the hole ho. Then, the X-Y alignment detection light beam proceeds to the half mirror M1 and the objective lens Ob to be led to a cornea C of the tested eye as a parallel light flux. A bright spot image (false image) is formed on the cornea C by the cornea reflection of the X-Y alignment detection light beam.

The X-Y alignment detection light beam reflected by the cornea C is half reflected by the half mirror M1 to reach the wavelength selection mirror M2. Then, the X-Y alignment detection light beam totally transmits the wavelength selection mirror M2 to be led to the wave selection mirror M3, which reflects a part of the X-Y alignment detection light beam to the X-Y alignment sensor Se1 and transmits the rest to the total reflective mirror M4.

The X-Y alignment sensor Se1 detects a positional difference in the X-Y direction with respect to the apparatus itself in a plane vertical to an optical axis of the object lens Ob, based on the position of the bright spot image formed on the cornea C of the tested eye E, where the X direction is defined as the left and right direction and Y direction is defined as the upward and downward direction with respect to the tested eye E.

The Z alignment detection light beam from the Z alignment detection light source Os2 is projected to the cornea C of the tested eye E from a diagonal direction. A bright spot image (virtual image) is formed on the cornea C owing to cornea reflection of the Z alignment detection light beam. The Z alignment detection light beam is reflected in the diagonal direction by the cornea C to arrive at the Z alignment sensor Se2. The Z alignment sensor Se2 detects a positional difference (in the optical axis direction of the object lens Ob) in the Z axis direction with respect to the apparatus itself of the tested eye E, based on the position of the bright spot image formed on the cornea C.

The alignment detection system 6 is used to automatically perform a precise alignment of the apparatus itself with respect to the tested eye E after a rough alignment of the apparatus itself with respect to the tested eye E is completed according to the anterior eye segment observation system 5.

Since the principle of alignment for the alignment detection system 6 is publicly well-known, the detailed explanation of the principle is omitted.

Low Magnification Ocular Fundus Photographing System 1

The low magnification ocular fundus photographing system 1 includes a low magnification photographing illumination light source (for example, a halogen lamp) Os3, a wavelength selection mirror 7, a low magnification photographing diopter compensation lens L1, a wave selection mirror M8, a total reflection mirror M9, and a low magnification photographing camera (mono-chrome camera) Ca2.

The low magnification photographing diopter compensation lens L1, moved backward and forward along the optical axis O1, is used for compensating a refractive error of an eyeball.

The wavelength selection mirror (dichroic mirror) M7 wholly transmits the light beam over wavelength $\lambda=800$ nm, and totally reflects the light beam between $\lambda=500$ nm and 700 nm. The wavelength selection mirror M7 is also used for a high magnification photographing illumination light source Os4. The wavelength selection mirror M8 totally reflects the light beam below wavelength $\lambda=800$ nm and wholly transmits the light beam over wavelength $\lambda=800$ nm.

Light of infrared component above wavelength $\lambda=860$ nm is used as a low magnification photographing illumination light beam. The light beam of the infrared component totally passes through the wavelength selection mirror M7 to reach the hole-made mirror M6, by which the light beam is reflected to the half mirror M1. Moreover, the light beam, after transmitting the half mirror M1, is condensed by the object lens Ob to be led to the ocular fundus Ef of the tested eye E as a annular illumination light flux, in which the ocular fundus Ef of the tested eye E is illuminated.

The illumination light beam reflected by the ocular fundus Ef is converged by the object lens Ob to pass through the half mirror M1 and the hole h0 of the hole-made mirror M6. Then, the illumination light beam is led to the low magnification photographing diopter compensation lens L1 by way of the alignment mirror M5. After the refractive error of the eyeball is compensated by the low magnification photographing diopter compensation lens L1, the illumination light beam is led to the total reflection mirror M9 through the wave selection mirror M8. After this, the illumination light beam is deflected to the low magnification photographing camera Ca2 by the total reflection mirror M9, by which an image of the low magnified ocular fundus is focused in the low magnification photographing camera Ca2.

The low magnification ocular fundus photographing system 1, which is an optical system that corresponds to a conventional ocular fundus camera, is used for observing the ocular fundus Ef in a wide visual field and for determining a photographing position when photographing the ocular fundus at high magnification.

Fixation Target Projection System 7

The fixation target projection system 7 includes a fixation light source Os5 and the wavelength selection mirror M8. The fixation light source Os5 is an LED that emits light of wavelength $\lambda=560$ nm. The fixation target light from the fixation light source Os5 is deflected to the low magnification photographing diopter compensation lens L1 by the wavelength selection mirror M8 to be led to the object lens Ob through the low magnification photographing diopter compensation lens L1, the alignment mirror M5, the hole ho of the hole-made mirror M6, and the half mirror M1. The objective lens Ob forms a light source image of the fixation target on the ocular fundus Ef. The examinee pays close attention to the fixation target. The gaze direction of the examined eye E is determined by the fixation target projection system 7.

The fixation light source Os5 is movably constructed in a plane perpendicular to the optical axis 02. Changing the gaze direction of the examined eye E by moving the fixation light source Os5 enables the low magnification ocular fundus photographing system 1 and the high magnification ocular fundus photographing system 2 to observe a predetermined position of the ocular fundus.

Wave Front Aberration Compensation System 8

The wave front aberration compensation system 8 includes a projection system and a light receiving system.

The projection system includes a wave front sensor light source Os6, a half mirror M10, a total reflection mirror M11, a wavelength selection mirror 12, a wave front compensation element (for example, a reflective type of deformable mirror) M12', an astigmatism compensation variable cross-cylinder Vcc, a wavelength selection mirror M13, a Y direction tracking mirror YTM1, an X direction tracking mirror XTM1, a wavelength selection mirror M14, a total reflection mirror M15, a wavelength selection mirror M16, and a high magnification photographing diopter compensation mirror M17. An optical element of one portion of the wave front aberration compensation system 8 is positioned in a optical path of the high magnification ocular fundus photographing system 2 to be used with an optical element of the high magnification ocular fundus photographing system 2.

The wave front sensor light source Os6 is used to illuminate a light beam of wavelength $\lambda=830$ nm to the ocular fundus Ef of the tested eye E. The half mirror has the characteristics of half transmittance and half reflection. The wavelength selection mirror M12 totally transmits light above wavelength $\lambda=800$ nm, and totally reflects light below wavelength $\lambda=800$ nm.

The astigmatism compensation variable cross-cylinder Vcc plays a role of compensating a spherical power, a cylindrical power, and an axis angle. The wavelength selection mirror M13 totally transmits light above wavelength $\lambda=860$ nm, and totally reflects light below wavelength $\lambda=860$ nm.

The wavelength selection mirror M14 totally transmits light above wavelength λ=860 nm, and totally reflects light below wavelength λ=860 nm. The wavelength selection mirror M16 totally transmits light above wavelength λ=860 nm, and totally reflects light below wavelength λ=860 nm, too.

A light beam of wavelength λ=830 emitted from the wave front sensor light source Os6 is reflected by the half mirror M10 to reach the total reflection mirror M11, which, in turn, reflects the light beam to the wavelength selection mirror M12. After passing through the wavelength selection mirror M12, the light beam of wavelength λ=830 reaches the wavelength selection mirror M13 via the wave front compensation element M12' and the astigmatism compensation variable cross-cylinder Vcc.

The light beam of wavelength λ=830 is reflected by the wavelength selection mirror M13 to arrive at the wavelength selection mirror M14 by way of the Y direction tracking mirror YTM1 and the X direction tracking mirror XTM1. Furthermore, the light beam of wavelength λ=830 is reflected by the wavelength selection mirror M14 to hit against the total reflection mirror M15, which sends out the light beam to the wavelength selection mirror M16.

The light beam of wavelength λ=830 is totally reflected by the wavelength selection mirror M16 to reach the objective lens through the high magnification photographing diopter compensation mirror M17, the wavelength selection mirror M2, and the half mirror M1. The objective lens projects a point light source image to the ocular fundus.

The light receiving system includes the half mirror M10, the total reflective mirror 11, the wavelength selection mirror M12, the wave front compensation element (deformable mirror) M12', the astigmatism compensation variable cross-cylinder Vcc, the wavelength selection mirror M13, the Y direction tracking mirror YTM1, the X direction tracking mirror XTM1, the wavelength selection mirror M14, the total reflection mirror M15, the wavelength selection mirror M16, a high magnification photographing diopter compensation mirror M17, and a wave front sensor Se3.

The wave front sensor Se3 includes a Hartmann's diaphragm having an aperture with numerous holes and a light receiver for detecting a position reached by each beam that has passed through the numerous holes. The wave front is detected based on the reached position by the beam on the light receiver of the wave front sensor Se3. The wave front sensor Se3 is publicly known.

The reflective light beam from the ocular fundus takes a reverse light path, that is, the reflective light beam passes through the objective lens, the half mirror M2, the wavelength selection mirror M2, the high magnification photographing diopter compensation mirror M17, the wavelength selection mirror M16, the total reflection mirror M15, the wavelength selection mirror M14, the X direction tracking mirror XTM1, the Y direction tracking mirror YTM1, the wavelength selection mirror M13, the astigmatism compensation variable cross-cylinder Vcc, the wave front compensation element M12', the wavelength selection mirror M12, and the total reflection mirror M11 to reach the half mirror M10, through which the reflective light beam is led to the wave front sensor Se3.

The wave aberration includes aberration caused by the tested eye. The aberration measured by the wave front sensor Se3 controls the wave front compensation element M12' to change its shape of the reflective surface. This compensates the wave aberration to compensate optical aberration of the tested eye.

For example, the opthalmologic apparatus in the prior art can take a picture of a cell about 5 μm in size. On the other hand, the opthalmologic apparatus in accordance with the present invention can photograph a cell about 2 μm in size.

Since there is a limit in compensation quantity of the wave front aberration the wave front compensation element M12' can perform, the high magnification photographing diopter compensation mirror M17 is moved in the direction of an arrow F-F to adjust an optical path from the wave front sensor Se3 to the ocular fundus Ef of the tested eye. This compensates most of the component of the spherical power (components of hyperopia and myopia) of refractive error of the tested eye E.

Rotational adjustment of a relative angle of a pair of cylindrical lens constituting the astigmatism compensation variable cross-cylinder Vcc and an overall angle compensates most of the astigmatism component of refractive error of the tested eye E.

High-degree aberration of aberration caused by refractive error of an eye ball cannot be removed by the high magnification photographing diopter compensation mirror M17 and the astigmatism compensation variable cross-cylinder Vcc. However, the high-degree aberration can be compensated by the wave front compensation element M12'. The wave front aberration compensation system 8 can eliminate all types of aberration except for color aberration and distortion aberration to produce a clear image even at higher magnification.

The X direction tracking mirror XTM1 and the Y direction tracking mirror YTM1 constitute the ocular fundus tracking control driver 9.

High Magnification Ocular Fundus Photographing System 2

The high magnification ocular fundus photographing system 2 is composed of an illumination system and an image receiving system. The illumination system includes the high magnification photographing illumination light source Os4 and the wavelength mirror M7.

The optical path of the image receiving system includes the wave front aberration compensation system 8 and the ocular fundus tracking control driver 9. The image receiving system includes a high magnification photographing camera Ca3 as a photographing device, an the image forming lens L2, the wavelength selection mirror M12, the wave front compensation element (deformable mirror) M12', the astigmatism compensation variable cross-cylinder Vcc, the wavelength selection mirror M13, the Y direction tracking mirror YTM1, the X direction tracking mirror XTM1, the wavelength selection mirror M14, the total reflection mirror M15, the wavelength selection mirror M16, the high magnification photographing diopter compensation mirror M17. A color CCD camera is used as the high magnification photographing camera Ca3.

A xenon lamp, for example, is used as the high magnification photographing illumination light source Os4. Light of wavelength λ=500 nm to 700 nm from the xenon lamp is used as the high magnification photographing illumination beam. The illumination beam of wavelength λ=500 nm to 700 nm from the xenon lamp is totally reflected by the wavelength selection mirror M7 to reach the hole-made mirror M6, by which the illumination beam is deflected. Then, the deflected illumination beam hits against the ocular fundus Ef of the tested eye as an annular light beam, by way of the half mirror M1 and the objective lens Ob.

The reflected illumination beam from the ocular fundus Ef is converged by the objective lens Ob and reflected to the wavelength selection mirror M2 via the half mirror M1. The illumination beam, which reached the wavelength selection mirror M2, proceeds to the high magnification photographing diopter compensation mirror M17, the wavelength selection mirror M16, the total reflection mirror M15, the wavelength selection mirror M14, the X direction tracking mirror XTM1, the Y direction tracking mirror YTM1, the wavelength selection mirror M13, the astigmatism compensation variable cross-cylinder Vcc, the wave front compensation element (deformable mirror) M12', and the wavelength selection mirror M12. Moreover, the illumination light is totally reflected by the wavelength selection mirror M12 to be led to the image forming lens L2, which enables magnification conversion by an electrically movable revolver. The illumination light reflected at the ocular fundus Ef is focused on a photographing surface of the high magnification photographing camera Ca3 through the image forming lens L2.

Ocular Fundus Tracking Control Driver 9

The ocular fundus tracking control driver 9, which shares a part thereof with a tracking detector 10, is used to dispose a photographic visual field of the high magnification ocular fundus photographing system 2 at a predetermined position of the ocular fundus Ef so that a gaze direction of the tested eye E is detected to follow a photographic direction of the high magnification ocular fundus photographing system 2 to the gaze direction of the tested eye E.

The use of the ocular fundus tracking control driver 9 enables an permanently still image of the ocular fundus to be formed on the high magnification photographing camera Ca3 without the influence of a fixation micro-movement of the tested eye. As a result, a clear image of the ocular fundus without a blur can be obtained even in a case where an observation or photographing at the level of a visual cell with optical resolution is needed.

The tracking detector 10 includes a visual line detection light source Os7, a half mirror 18, an X direction scanning mirror XTM2, a Y direction scanning mirror YTM2, a visual line detection optical axis offset mirror M19, a pinhole plate Pi, and a visual line (direction) detection sensor (light receiving element) Se4.

The pinhole plate Pi is provided in front of the visual line detection sensor Se4. An LED that emits near infrared of wavelength $\lambda=945$ nm is used as the visual line detection light source Os7. The near infrared is not used for taking a picture.

Light of the near infrared from the visual line detection light source Os7 is deflected by the half mirror 18 to the Y direction scanning mirror YTM2 and then to the X direction scanning mirror XTM2, by which the light of the near infrared is deflected to the wavelength selection mirror M13.

After the light of the near infrared of $\lambda=945$ nm totally transmits the wavelength selection mirror M13, it proceeds to the wavelength selection mirror M14 via the Y direction tracking mirror YTM1 and the X direction tracking mirror XTM1.

After the light of the near infrared of $\lambda=945$ nm passes through the wavelength selection mirror M14, it goes to the visual line detection optical axis offset mirror M19, by which the light of the near infrared is deflected to the wavelength selection mirror M16. After passing through the wavelength selection mirror M16, the light of the near infrared is projected to the ocular fundus Ef of the tested eye E by way of the high magnification photographing diopter compensation mirror M17, the wavelength selection mirror M2, the half mirror M1, and the objective lens Ob.

A beam from the visual line detection light source Os7 should illuminate a wide range of predetermined positions on the ocular fundus Ef. That is, an area of the ocular fundus to be illuminated should be smaller than or equal to an area optically covered by the visual line detection sensor Se4.

A wide range of areas can be uniformly illuminated by using an optical structure for the ocular fundus illumination system that is used for a general ocular fundus camera.

The pinhole plate Pi is placed at a conjugate position of the ocular fundus Ef. A photo diode, for example, is used as the visual line direction detection sensor Se4. The wavelength selection mirror M16 is used to separate a photographing optical path of the high magnification ocular fundus photographing system 2 from a detection optical path of a gaze direction detection axis.

As an example of the visual line direction detection sensor Se4, an APD (Avalanche Photo Diode) except for a photo diode (including a PIN photo diode), or photomultiplier, each having high sensitivity, can be used dependent upon the need.

The visual line detection optical axis offset mirror M19 is used to move the gaze direction detection axis, and is disposed out of the photographing optical path of the ocular fundus and within an optical path of the tracking detector 10 for the visual line direction detection.

That is, the visual line detection optical axis offset mirror M19 is slanted in the two dimensions (X and Y directions), a position on the ocular fundus as a tracking target is arbitrarily selected.

In accordance with the wavelength selection mirrors M14 and M16, the visual line detection optical axis offset mirror M19 bends only near infrared of wavelength $\lambda=945$ nm to move the detection axis of the gaze direction. This does not produce any influence on the photographing optical axis with respect to the ocular fundus.

The X direction scanning mirror XTM2 and the Y direction scanning mirror YTM2 play a function of scanning a pinhole corresponding region (reflective region) on the ocular fundus that is conjugate to a pinhole on the pinhole plate Pi. The pinhole corresponding region is moved so that the scanning draws, for example, an oval locus on the ocular fundus. The idea of oval connotes a circle. The pinhole corresponding region (reflective region) is a visual field for the visual line direction detection.

For example, when vibration directions of the X direction scanning mirror XTM2 and the Y direction scanning mirror YTM2 are orthogonal to each other and the two mirrors are vibrated at the same frequency and amplitude with a 90-degree phase difference, a circular scanning can be carried out.

Figure 3:
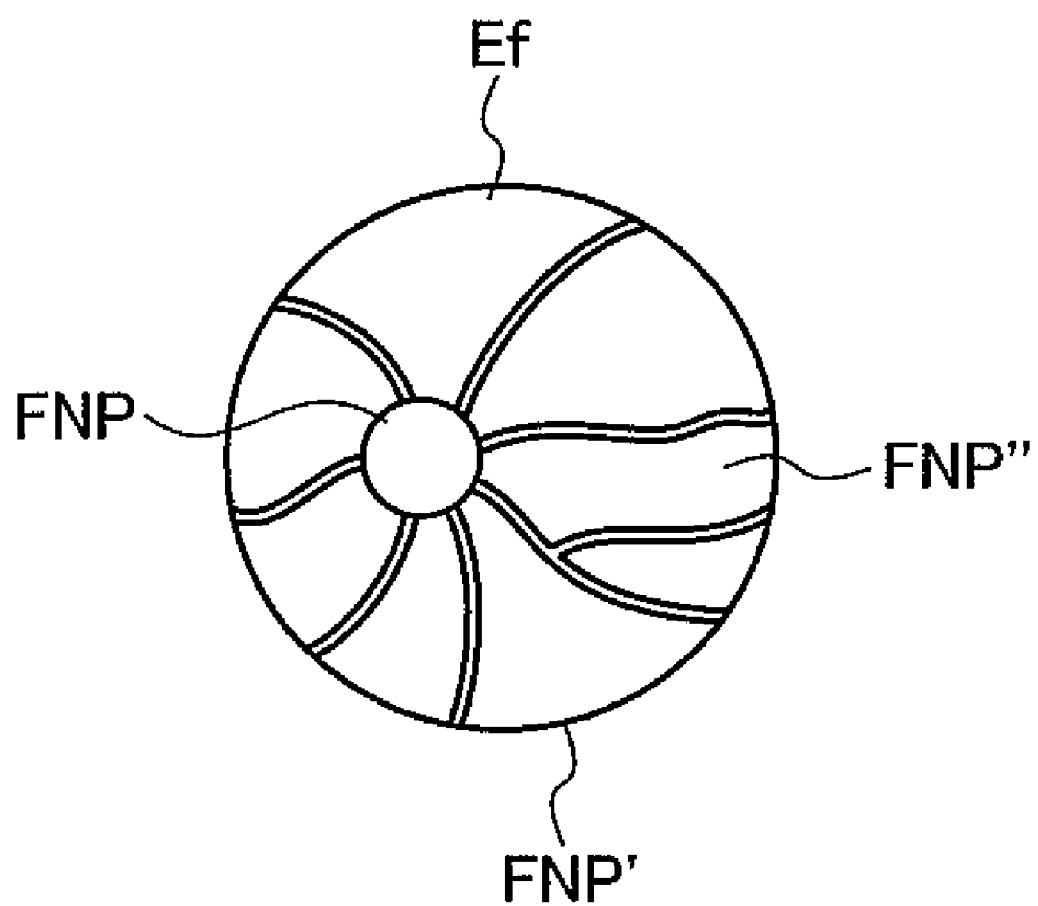
FIG. 3 is an illustrative view of an ocular fundus of a tested eye in FIG. 1.

The tracking target for the visual field of the visual line direction detection may be approximately circular. Typical of the tracking target are an optic disc FNP shown in FIG. 3, a macula fovea, an intersection of blood vessels, a white spot on the ocular fundus and a drusen.

One of photographing targets is a cell in the ocular fundus. When the cell (on order of micron) in the ocular fundus is photographed as a photographing target, an optic disc FNP (on order of millimeter) may be selected as a tracking target.

Figure 4A:
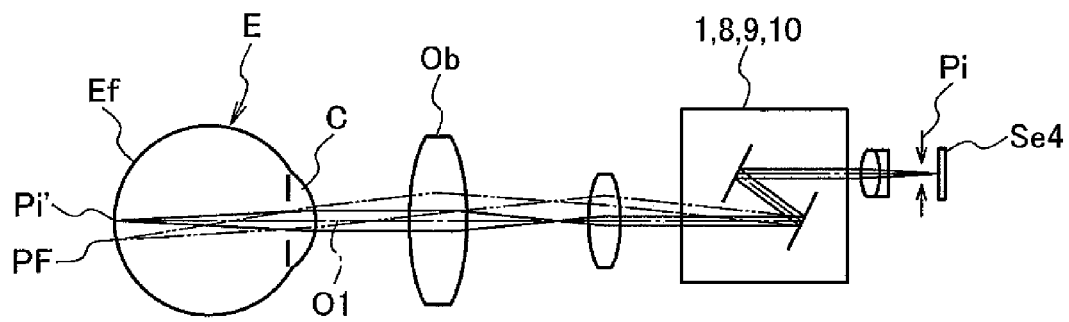
FIG. 4A is an illustrative view of an optical path showing an offset for an ocular fundus photographing beam and a detection beam, where tracking control is explained for the ocular fundus of the tested eye shown in FIG. 1.

FIG. 4A is an illustrative view of an optical path showing an offset for an ocular fundus photographing beam and a detection beam, where tracking control is explained for the ocular fundus of the tested eye shown in FIG. 1.

As shown by the solid lines in FIG. 4A, light of wavelength $\lambda=945$ nm from a pinhole corresponding area Pi' on the ocular fundus Ef proceeds to the pinhole plate Pi by way of the objective lens Ob, the half mirror M1, the wavelength selection mirror M2, the high magnification photographing diopter compensation mirror M17, the wavelength selection mirror M16, the visual line detection optical axis offset mirror M19, the X direction tracking mirror XTM1, the Y direction tracking mirror YTM1, the wavelength selection mirror M13, the X direction scanning mirror XTM2, the Y direction scanning mirror YTM2, and the half mirror M18. The light that has passed through the pinhole of the pinhole plate Pi is received by the visual line detection sensor Se4.

PF represents a tracking target when a cell is examined. For example, as a tracking target, the optic disc FNP can be selected.

The scanning is carried out to move along an edge FNP' of the optic disc FNP as a tracking target. The adjustment of moving along the edge FNP' is made based on an adjustment of a tilt of the visual line detection optical axis offset mirror M19

Figure 4B:
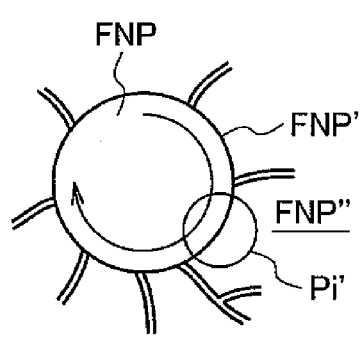
FIG. 4B is an illustrative view of a locked state in which a tracking target is locked owing to tracking by using a pinhole corresponding region.

FIG. 4B is an illustrative view of a locked state in which a tracking target is locked owing to tracking by using the pinhole corresponding region.

As shown in FIG. 4B, the tracking target is the optic disc FNP. The tracking target is brighter than the ocular fundus area FNP'''. When the edge FNP' is identical to a circular locus drawn by the pinhole corresponding region Pi', an output from the visual line detection sensor Se4 does not change in the course of scanning.

Figure 4C:
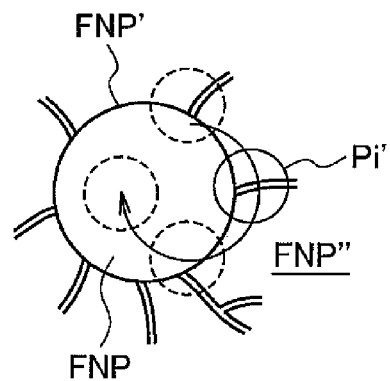
FIG. 4C is an illustrative view of a state in which the tracking target to be detected by the pinhole corresponding region is shifted to the right.

FIG. 4C is an illustrative view of a state in which the tracking target to be detected by the pinhole corresponding region is shifted to the right.

On the contrary to FIG. 4B, as shown in FIG. 4C, the circular locus drawn by the pinhole corresponding region Pi' is shifted to the right with respect to the optic disc FNP. An average output for one period of the output from the visual line detection sensor Se4 has no variation because most of the pinhole corresponding region Pi' overlaps the optic disc FNP. However, the output of the visual line detection sensor Se4 when the pinhole corresponding region Pi' is in the right is different from that when the pinhole corresponding region Pi' is in the left.

Figure 4D:
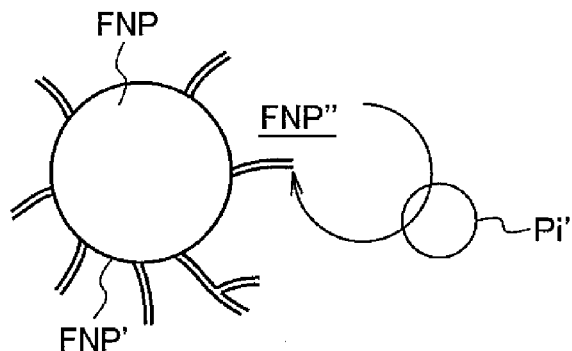
FIG. 4D is an illustrative view of a state in which the tracking target to be detected by the pinhole corresponding region is unlocked.

FIG. 4D is an illustrative view of a state in which the tracking target to be detected by the pinhole corresponding region is unlocked.

As shown in FIG. 4D, the locus drawn by the pinhole corresponding region Pi' is away from the optic disc FNP and in the ocular fundus region FNP'''. The average output for one cycle of the visual line detection sensor Se4 when the locus is in the ocular fundus region FNP''' is lower than that when the edge FNP' is identical to a circular locus drawn by the pinhole corresponding region Pi'.

The output of the visual line detection sensor Se4 is applied to a process circuit that will be discussed. The process circuit adjusts the X direction tracking mirror XTM1 and the Y direction tracking mirror YTM1 so that the average outputs are equal in the up and down and left and right directions According to this, as shown in FIG. 4B, the optic disc FNP, a tracking target, is locked, which executes tracking with respect to the ocular fundus Ef. When, for example, tracking is performed in the left and right directions, the process circuit drives the X direction tracking mirror XTM1 and the Y direction tracking mirror YTM1 for tracking adjustment to the ocular fundus Ef, in order that with respect to an amplitude center of a fixation micro-movement for the ocular fundus Ef, an average output from the visual line direction detection sensor Se4 obtained by scanning the left half is equal to that obtained by scanning the right half. The details for the control will be described later as an explanation of control-related signal processing.

An explanation has been made so far regarding the optic disc FNP as a tracking target. When the tracking target is darker than the ocular fundus region FNP''' like a macula fovea, tracking process may be performed by treating as a reference an average output of the darker region. Namely, the tracking target should be distinguished between a specific area and the rest of it in terms of brightness.

An explanation is given assuming that the scanning locus regarding the tracking target is elliptic. However, the scanning locus is not limited to this, and may be square or triangular.

In this way, the gaze direction for the tested eye E is detected, according to the output from the visual line direction detection sensor Se4 that responds to the scanning locus drawn by the pinhole corresponding region Pi' on the ocular fundus Ef. Controlling the X direction tracking mirror XTM1 and the Y direction tracking mirror YTM1 based on the detection result enables a photographing position for the high magnification ocular fundus photographing to follow the fixation micro-movement.

In other words, a small-sized specific position should be determined as a photographing target, and a specific object adjacent to the photographing target should be selected as a tracking target. In the case, when the photographing target is small-sized, the optical system for the eye of human beings cannot be regarded as perfect, and instead should be handled as imperfect. Owing to this, a wave front compensation element M12' should be inserted in the optical path.

Under the structure, when a cell is selected as the photographing target, it is possible to know a condition of the cell, for example, the condition that the cell is now sick or will be sick.

An explanation is made in which the wavelength of light in the tracking detector 10 is different from that of the illumination light for the low magnification ocular fundus photography. The reflective light derived from the illumination light for the low magnification ocular fundus photography may be used to detect the gaze direction. In the case, the visual line detection light source Os7 should not be provided as an exclusive light source.

Control-Related Signal Processing

Figure 5A:
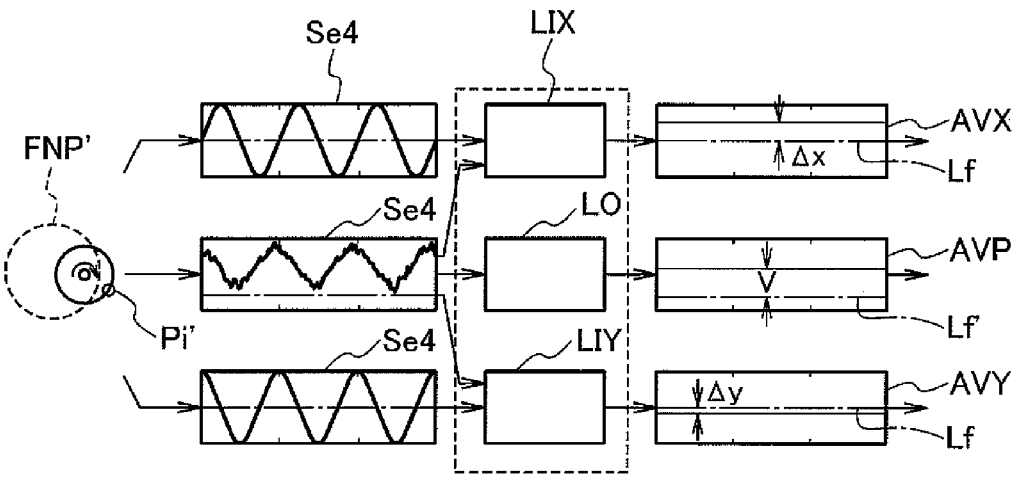
FIG. 5A is an illustrative view of a state in which the tracking target to be detected by the detection beam is shifted to the right, where the principle of locking operation for the tracking target in the ocular fundus shown in FIGS. 4A to 4D is explained.
Figure 5B:
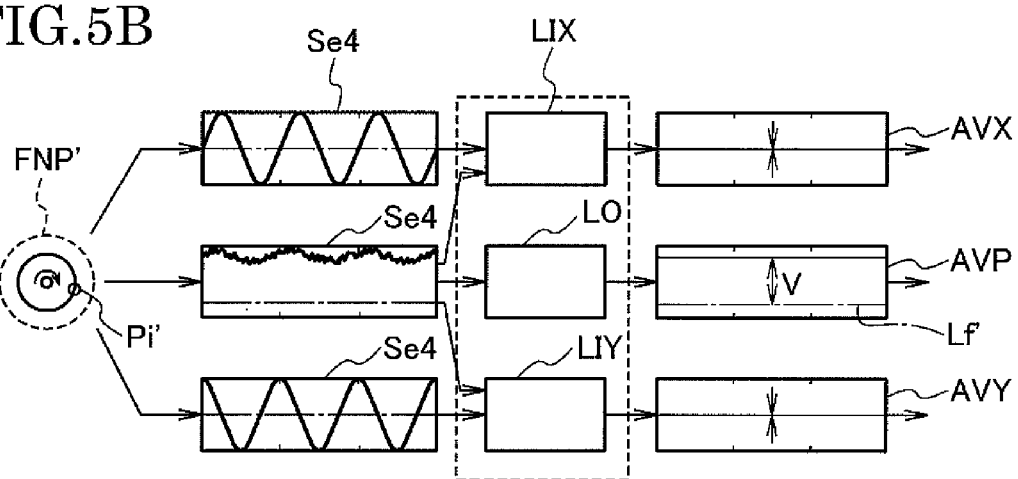
FIG. 5B is an illustrative view of a state in which the tracking target to be detected by the detection beam is locked by tracking.
Figure 5C:
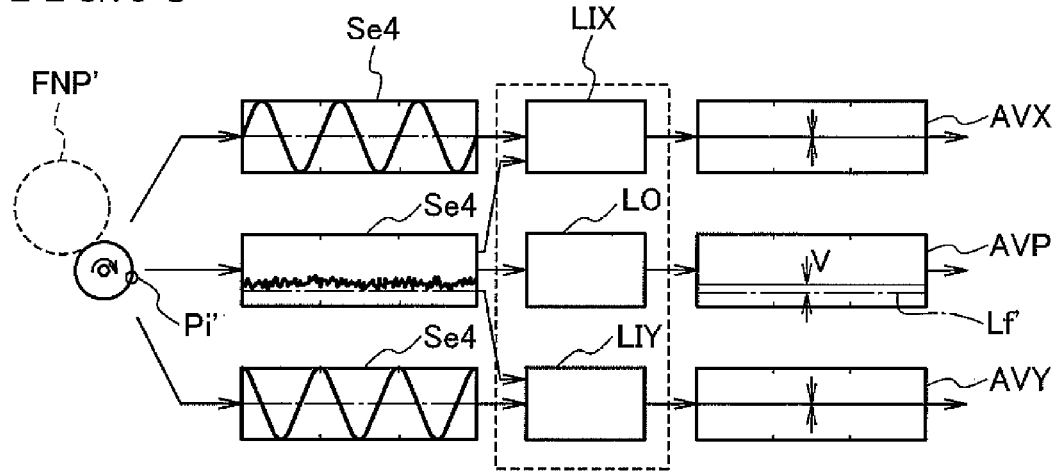
FIG. 5C is an illustrative view of a state in which the tracking target to be detected by the detection beam is shifted to the right (out of lock).

The control circuit performs a series of signal processing shown in FIG. 5A-5C. For the convenience of explanation, a current-voltage converter for converting an output current from the visual line direction detection sensor Se4 to a voltage and an amplifier for amplifying a signal level are omitted.

FIG. 5A is an illustrative view of a state in which the tracking target to be detected by the detection beam is shifted to the right, where the principle of locking operation for the tracking target in the ocular fundus shown in FIGS. 4A to 4D is explained. FIG. 5B is an illustrative view of a state in which the tracking target to be detected by the detection beam is locked by tracking. FIG. 5C is an illustrative view of a state in which the tracking target to be detected by the detection beam is shifted to the right (out of lock).

The control circuit includes lock-in detectors LIX and LIY, and a low-pass filter Lo. As shown in FIGS. 5A-5D, the pinhole corresponding region Pi' with respect to the tracking target is drawing a scanning locus at the same frequency, having 90-degree phase difference between the X direction and the Y direction.

The X direction tracking mirror XTM1 is scanned by a sine curve, while the Y direction tracking mirror YTM1 is scanned by a cosine curve. The sine curve input is applied to the lock-in detector LIX, and the cosine curve input to the lock-in detector LIY.

The outputs from the visual line detection sensor Se4 are furnished to the lock-in detectors LIX and LIY, synchronous with the scanning. The output from the visual line detection sensor Se4 is also applied to the low-pass filter Lo. The lock-in detector LIX detects the X direction component, while the lock-in detector LIY detects the Y direction component.

Each output of the lock-in detectors LIX and LIY and the low-pass filter Lo are furnished to average circuits AVX, AVY, and AVP, respectively. The average circuit AVX is used to detect a variation ΔX in the X direction, the average circuit AVY a variation ΔY in the Y direction, and the low-pass filter Lo an average output V.

As shown in FIG. 5A, when the scanning locus of the pinhole corresponding region Pi' is on the right side, the difference ΔX in the X component with respect to a reference level Lf is larger than the difference ΔY in the Y component with respect to a reference level Lf. The average output V of the low-pass filter Lo is appropriate with respect to a reference level Lf'.

As shown in FIG. 5B, when the scanning locus of the pinhole corresponding region Pi' is identical to the tracking target FNP, the difference ΔX in the X component with respect to the reference level Lf and the difference ΔY in the Y component with respect to the reference level Lf are minimal. In contrast, the average output V of the low-pass filter Lo is maximum with respect to a reference level Lf', and becomes a signal to prove the presence of the target (target presence signal).

As shown in FIG. 5C, when the scanning locus of the pinhole corresponding region Pi' is away from the tracking target FNP, the difference ΔX in the X component with respect to the reference level Lf, the difference ΔY in the Y component with respect to the reference level Lf, and the average output V of the low-pass filter Lo are all minimal.

Each output of the lock-in detectors LIX and LIY and a low-pass filter Lo is applied to an input of an X direction tracking mirror driver and an input of an Y direction tracking mirror driver (not shown). The X direction tracking mirror XTM1 and the Y direction tracking mirror YTM1 are driven, so that the difference ΔX in the X component with respect to the reference level Lf and the difference ΔY in the Y component with respect to the reference level Lf are both minimal, and the target presence signal is over a predetermined value. This constructs a tracking servo system.

Since the optical path of the high magnification ocular fundus photographing system 2 includes the same X direction tracking mirror XTM1 and Y direction tracking mirror YTM1, a photographing range follows a fixation micromovement of the eyeball and is always fixed at a predetermined position.

Because the tracking detector 10 offsets a visual line detection beam shown by the solid lines and a reflective beam from the photographing portion PF shown by the dotted lines in FIG. 4A, a desired photographing portion PF on the ocular fundus can be photographed.

Operation Procedures

A photographing magnification of the high magnification ocular fundus photographing system 2 should be selected in accordance with a purpose. At the same time, based on measurement information of the tested eye, astigmatism compensation quantity and compensation direction are set at the astigmatism compensation variable cross-cylinder Vcc.

The face of an examinee should be placed on a chin rest (not shown) of the apparatus, and his forehead should be put at a forehead receiver, in order to fix the face of the examinee. The eye E to be tested is determined as to where the eye is disposed with respect to the apparatus.

An examiner observes an anterior eye segment through the anterior eye segment observation system 5, and matches a pupil of the tested eye E with the optical axis 01 of the apparatus regarding their positions by a manual operation. Then, the apparatus is moved along the optical axis 01 to the examinee's side. According to the manual adjustment, when a position of the tested eye E is within a range of predetermined alignment, the alignment detection system 6 automatically operates to perform an alignment of the apparatus with respect to the tested eye E.

The optical axis 01 of the apparatus is precisely aligned with respect to the tested eye E, the examinee can inspect the fixation light source Os5 within the apparatus. Examinee's close observation of the fixation light source Os5 fixes a gaze direction of the tested eye E The examiner operates the low magnification photographing diopter compensation lens L1 to focus on the ocular fundus. The high magnification photographing diopter compensation mirror M17 is moved associated with the low magnification photographing diopter compensation lens L1 to be shifted to the focused position.

Figure 6:
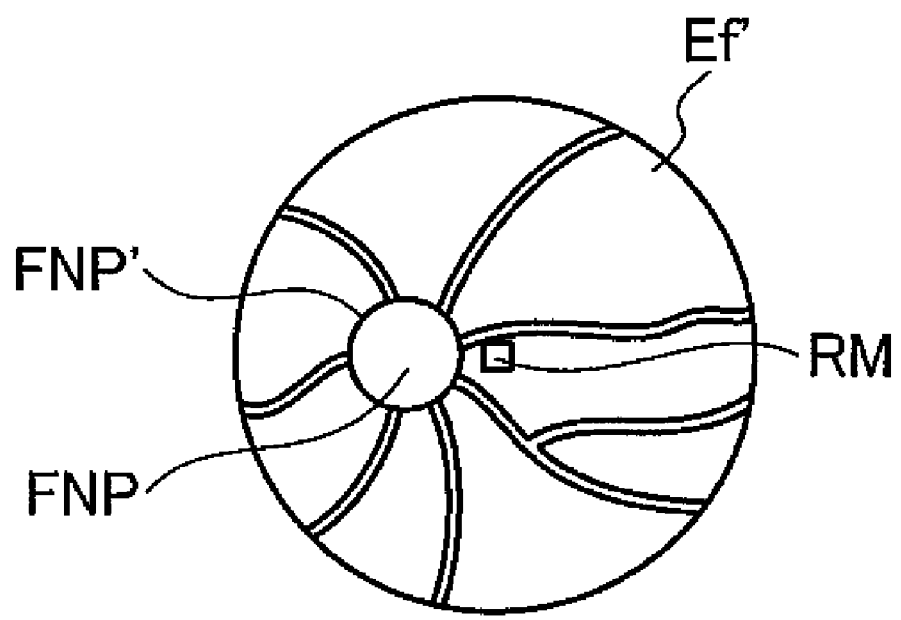
FIG. 6 is an illustrative view of the ocular fundus photographing image of the tested eye shown in FIG. 1.

The examiner observes an ocular fundus image Ef' on a monitor of the low magnification photographing system 1. As shown in FIG. 6, a square mark RM, which represents a photographing position to be photographed by the high magnification ocular fundus photographing system 2, is displayed in the ocular fundus image Ef' observed by the low magnification photographing system 1. The examiner can confirm the photographing position the high magnification ocular fundus photographing system 2 takes a picture of, by inspecting the square mark RM.

When the photographing position the high magnification ocular fundus photographing system 2 photographs is not a desired position, the examiner moves the fixation light source Os5 to shift the gaze direction of the examinee. This enables a desired photographing position to be at the square mark RM. In this case, since a positional relationship between a position of a cornea reflective image and a pupil of the examined eye E varies according to a shift of the gaze direction, the alignment optical system 6 compensates this. When the ocular fundus image observed by the low magnification photographing system 1 is stored by a storing device (not shown), it can be later confirmed where on the ocular fundus Ef the photographing position, which the high magnification ocular fundus photographing system 2 has photographed, belongs to.

A projection area of a beam from the visual line detection light source Os7 of the tracking detector 10 can be observed, by using the low magnification photographing system 1.

When the visual line detection optical axis offset mirror M19 is adjusted, slanted in two-degree dimensions, a tracking position of the ocular fundus Ef can be offset at a desired position.

An offset adjustment is made, by observing a projection position of a beam from the visual line detection light source Os7. When a movement position of the visual line detection light axis decided by a tilt angle of the visual line detection optical axis offset mirror M19 is overlapped with the ocular fundus image Ef' to be displayed, an offset adjustment based on the display can be performed. By analyzing the ocular fundus image Ef', a slant angle of the visual line detection optical axis offset mirror M19 may be adjusted so that a visual line detection optical axis matches with a desired position of the optic disc FNP After setting a photographing position and a tracking target position by the high magnification ocular fundus photographing system 2, the opthalmologic apparatus performs the compensation by the wave front aberration compensation system 8 and the ocular fundus tracking control.

The high magnification ocular fundus photographing system 2 can obtain a clear image at the level of a visual cell in which high-degree aberration of the tested eye E is compensated, according to the aberration compensation the wave front aberration compensation system 8. In addition, tracking control of the ocular fundus can provide a ocular fundus image at the level of a visual cell without a blur in spite of a fixation micro-movement.

With regard to diopter compensation of the high magnification ocular fundus photographing system 2, the examiner may provide a setting device that adjusts a small amount of offset concerning the focused surface automatically followed by a diopter compensation apparatus (not shown). The setting device for the offset adjustment is used to set which portion of the ocular fundus should be photographed in the deep direction regarding the depth of field of the high magnification ocular fundus photographing system 2.

When the examiner pushes a photographing switch, the control circuit observes the state of each optical system. If, for example, an extraordinary event such as "off tracking" has not occurred, the examiner emits the high magnification photographing illumination light source Os4 to take a picture by using the high magnification ocular fundus photographing system 2.

Photographed data is, for example, recorded in a film or filed as an electronic image. At the same time, the following are also recorded: which is photographed, left or right eye; diopte of let and right eyes; the astigmatism compensation variable cross-cylinder Vcc; the wave front compensation element M12'; photographing magnification; offset of the tracking target and photographing position; and images of the low magnification ocular fundus photographing system 1.

In order to compensate a focal depth of the high magnification ocular fundus photographing system 2, which is very shallow, as an additional function, by a trigger based on a one-time photographic switch operation or by triggers based on plural-time photographic switch operations, an image is taken that is derived by shifting backward and forward the focus for the high magnification photographing, at a step of the focal depth of the high magnification ocular fundus photographing system 2.

The so-called focus bracketing photographing can provide a clear ocular fundus image, even in photographing the ocular fundus image Ef' having ruggedness.

In the embodiments, tracking control is carried out by scanning the pinhole corresponding region (infinitesimal region) Pi'. However, another structure may be employed in which an infinitesimal spot-type illumination detection beam is projected to the pinhole corresponding region (infinitesimal region) Pi' for scanning and a variation of light quantity of reflective light associated with the detection beam is detected.

According to the present invention, although an effective aperture of a photographing lens for an ocular fundus high magnification observation is minimum, a detection axis of a gaze direction can be adjusted to a large extent, even to an area outside the ocular fundus high magnification observation. Accordingly, an ocular fundus can be photographed at high magnification and with high resolution.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An ophthalmologic apparatus comprising:
    an ocular fundus photographing system that forms an image of an ocular fundus of a tested eye on a photographing apparatus based on a reflective beam from the ocular fundus; and
    an ocular fundus tracking controller that detects a light beam from the ocular fundus, reflected at a reflective region of an illuminated region on the ocular fundus to detect a gaze direction of the tested eye, and performs tracking with respect to the ocular fundus based on the detection result of the gaze direction, the ocular fundus tracking controller comprising:
        a scanning mirror for scanning an area on which a detection beam projected on the ocular fundus is detected or a reflective beam from the ocular fundus is detected;
        a tracking mirror for controlling tracking to the ocular fundus;
        an objective lens disposed opposite to the tested eye; and
        an offset mirror positioned between the objective lens and the tracking mirror outside of a photographing optical path for the ocular fundus, for adjusting a detection axis of the gaze direction.

2. An ophthalmologic apparatus as recited in claim 1, wherein the reflective beam from the ocular fundus proceeds to the photographing apparatus not through the offset mirror after entering the tracking mirror.

3. An ophthalmologic apparatus as recited in claim 1, wherein the ocular fundus photographing system includes a compensation optical system for compensating optical aberration of the tested eye.

4. An ophthalmologic apparatus as recited in claim 1, further comprising an illumination beam for photographing the ocular fundus and a detection beam for detecting the gaze direction of the tested eye, the illumination beam having a wavelength that is different from that of the detection beam.

* * * * *